United States Patent
Rozzell et al.

(10) Patent No.: US 6,822,116 B2
(45) Date of Patent: Nov. 23, 2004

(54) METHOD FOR PRODUCING D-ALLO-ISOLEUCINE

(75) Inventors: J. David Rozzell, Burbank, CA (US); Dunming Zhu, Arcadia, CA (US)

(73) Assignee: BioCatalytics, Inc., Pasadena, CA (US)

( * ) Notice: Subject to any disclaimer, the term of this patent is extended or adjusted under 35 U.S.C. 154(b) by 224 days.

(21) Appl. No.: 10/165,495

(22) Filed: Jun. 7, 2002

(65) Prior Publication Data

US 2003/0219879 A1 Nov. 27, 2003

Related U.S. Application Data

(60) Provisional application No. 60/383,067, filed on May 24, 2002.

(51) Int. Cl.$^7$ ............................................. C07C 229/00
(52) U.S. Cl. ....................................................... 562/575
(58) Field of Search .......................................... 562/575

(56) References Cited

U.S. PATENT DOCUMENTS 5,565,344 A  10/1996  Nanba et al.
6,310,242 B1  10/2001  Noda et al.

FOREIGN PATENT DOCUMENTS

EP  0 937 705 A2  8/1999

OTHER PUBLICATIONS

Garcia, M.J. and Azerad R., Production of ring-substituted D-phenylglycines by microbial or enzymatic hydrolysis/deracemisation of the corresponding DL-hydantoins, *Tetrahedron: Asymmetry, 1997*, pp. 85–92, vol. 8, No. 1, Elsevier Science Limited, Great Britian.

Keil, O, et al., New Hydantoinases from Thermophilic Microorganisms–Synthesis of Enantiomerically Pure D–Amino acids, *Tetrahedron: Asymmetry, 1995*, pp. 1257–1260, vol. 6, No. 6, Elsevier Science Ltd., Great Britain.

*Primary Examiner*—Paul J. Killos
(74) *Attorney, Agent, or Firm*—Christie, Parker & Hale LLP

(57) ABSTRACT

A method for producing D-allo-isoleucine is provided. The method comprises converting L-isoleucine to the corresponding hydantoin. A mixture containing the hydantoin is contacted with a D-hydantoinase to stereoselectively hydrolyze any D-allo-isoleucine hydantoin in the mixture to the corresponding N-carbamoyl-D-allo-isoleucine. The N-carbamoyl-D-allo-isoleucine is decarbamoylated to produce D-allo-isoleucine. Preferably the contacting of the hydantoin with a D-hydantoinase is carried out under conditions permitting the simultaneous epimerization of the chiral center at C-5 of the hydantoin.

17 Claims, No Drawings

METHOD FOR PRODUCING D-ALLO-ISOLEUCINE

CROSS-REFERENCE

This application claims priority to U.S. Provisional Application No. 60/383,067, filed May 24, 2002, the entire disclosure of which is incorporated herein by reference.

FIELD OF THE INVENTION

This invention relates to methods for producing D-allo-isoleucine in high stereochemical purity.

BACKGROUND

Unnatural or non-proteinogenic amino acids, which are structural analogs of the naturally-occurring amino acids that are the constituents of proteins, have important applications as pharmaceutical intermediates. For example, the anti-hypertensives ramipril, enalapril, benazapril, and prinivil are all based on L-homophenylalanine; certain second generation pril analogs are synthesized from p-substituted-L-homophenylalanine. Various β-lactam antibiotics use substituted D-phenylglycine side chains, and newer generation antibiotics are based on aminoadipic acid and other UAAs. The unnatural amino acid L-tert-leucine has been used as a precursor in the synthesis of a number of different developmental drugs.

Unnatural amino acids are used almost exclusively as single stereoisomers. Since unnatural amino acids are not natural metabolites, traditional production methods for amino acids based on fermentation cannot generally be used since no metabolic pathways exist for their synthesis. Given the growing importance of unnatural amino acids as pharmaceutical intermediates, various methods have been developed for their enantiomerically pure preparation. Commonly employed methods include resolutions by diastereomeric crystallization, enzymatic resolution of derivatives, and separation by simulated moving bed (SMB) chiral chromatography. These methods can be used to separate racemic mixtures, but the maximum theoretical yield is only 50%.

The amino acid isoleucine poses special problems due to the presence of a second chiral center. Four distinct diastereomers exist for the constitutional carbon skeleton of isoleucine, consisting of two enantiomeric pairs: L-isoleucine, D-isoleucine, L-allo-isoleucine, D-allo-isoleucine, having the (2S,3S), (2R,3R), (2S,3R), and (2R, 3S) absolute configurations, respectively. The naturally-occurring L-isoleucine can be produced by fermentation, taking advantage of the existing metabolic pathway to introduce both chiral centers. Production of the other isoleucine diastereomers is more difficult, however. Separation of an equimolar mixture of the four diastereomers, which is extremely difficult and costly due to the chemical similarity of the compounds, can produce only a maximum theoretical yield of 25% of any single diastereomer, and in practice it is likely much lower. Synthesis of a racemate in which the relative stereochemistry of the two chiral centers is controlled will still only permit a maximum theoretical yield of 50% when the enantiomers are separated. Thus, an efficient method for preparation of a single diastereomer of D-isoleucine or D- or L-allo-isoleucine in high stereochemical purity would be highly desirable.

The present invention is directed toward a method for the preparation of D-allo-isoleucine, or (2R,3S)-2-amino-3-methylpentanoic acid, which has applications principally as a pharmaceutical intermediate and as a chemical for medical and biochemical research. Relatively few methods for the preparation of D-allo-isoleucine have been reported. Resolution of a racemate of allo-isoleucine has been accomplished [W. A. Hoffmann and A. W. Ingersoll, J. Am. Chem. Soc., 73, 3366(1951)]. This process requires conversion of racemic allo-isoleucine to the N-acetyl derivative, followed by diastereomeric crystallization using quinine as the resolving agent. The maximum theoretical yield is only 50%, and the racemate of allo-isoleucine is not itself readily available. Separation of the D-allo-isoleucine from a mixture of L-isoleucine and D-allo-isoleucine has also been accomplished in various ways, but all known methods require the epimerization of L-isoleucine to a mixture of L-isoleucine and D-allo-isoleucine, followed by the preparation of derivatives that can then be separated. Such methods include the recrystallization of the N-formyl derivative from methyl ethyl ketone (Dow Chemical, British Patent No. 704983); protection by conversion to the carbobenzyloxy or t-butyloxycarbonyl derivative, followed by separation relying on the difference in solubilities of salts made from optically pure 1-phenylethyl amine (G. Fluoret, S. H. Nagasawa, J. Org. Chem., 40, 2635 (1975)); and selective hydrolysis of the N-acetyl derivative of N-acetyl-L-isoleucine using an enzyme, followed by recovery of the remaining N-acetyl D-allo-isoleucine (P. Lloyd-Williams et al., J. Chem. Soc., Perkin Trans. I, Vol. 1994, (1969)). In all of these methods the maximum theoretical yield is 50%, but due to the multiple steps required and the inherent losses in the separation of diastereomers, actual yields are far lower.

More recently, Noda et al., in U.S. Pat. No. 6,310,242, have reported a method in which D-allo-isoleucine is separated from an epimeric mixture with L-isoleucine using a tartaric acid derivative by the formation of a complex, which is precipitated and decomposed in alcohol. An alternative uses a selective precipitation of the L-isoleucine derivative. Again, as a separation of stereoisomers, the maximum theoretical yield is 50%, and the actual yields were lower. It is also important to point out that the tartaric acid derivatives used were not readily available and relatively expensive to produce. In an improvement of this method, Noda and coworkers describe the use of the same tartaric acid to form a complex with D-allo-isoleucine in the presence of a C1 to C5 saturated fatty acid and salicylaldehyde. The reaction was carried out in an inert solvent that does not substantially dissolve amino acids. The reported optical purity was 94.6%. A method that achieves closer to 100% optical purity would be preferable and desirable.

SUMMARY OF THE INVENTION

The invention is directed to methods for producing D-allo-isoleucine. In one embodiment, the method for producing D-allo-isoleucine comprises converting L-isoleucine to the corresponding hydantoin. A mixture containing the hydantoin is contacted with a D-hydantoinase to stereoselectively hydrolyze any D-allo-isoleucine hydantoin in the mixture to the corresponding N-carbamoyl-D-allo-isoleucine. The conversion of L-isoleucine to the corresponding hydantoin may result in an epimeric hydantoin mixture containing at least detectable amounts of both L-isoleucine hydantoin and D-allo-isoleucine hydantoin. Accordingly, as used herein, the terminology "corresponding hydantoin" includes such epimeric hydantoin mixtures.

Preferably in the claimed method the contacting of the hydantoin with a D-hydantoinase is carried out under conditions permitting the simultaneous epimerization of the chiral center at C-5 of the hydantoin. As discussed further below, the simultaneous epimerization permits the reaction to be carried out to substantial completion so that L-isoleucine hydantoin is converted to N-carbamoyl-D-allo-isoleucine. The N-carbamoyl-D-allo-isoleucine is then decarbamoylated to produce D-allo-isoleucine.

In another embodiment, the invention is directed to a method for producing D-allo-isoleucine comprising first epimerizing L-isoleucine to a mixture of L-isoleucine and D-allo-isoleucine. The mixture of L-isoleucine and D-allo-isoleucine is converted to the corresponding hydantoin mixture containing L-isoleucine hydantoin and D-allo-isoleucine hydantoin. The hydantoin mixture is contacted with a D-hydantoinase under conditions permitting the stereoselective hydrolysis of only the D-allo-isoleucine hydantoin to the corresponding N-carbamoyl-D-allo-isoleucine. The N-carbamoyl-D-allo-isoleucine can then be decarbamoylated to produce D-allo-isoleucine.

In yet another embodiment, the invention is directed to a method for producing N-carbamoyl-D-allo-isoleucine. The method comprises converting L-isoleucine to the corresponding hydantoin and contacting a mixture containing the L-isoleucine hydantoin with a D-hydantoinase to stereoselectively hydrolyze any D-allo-isoleucine hydantoin in the mixture to the corresponding N-carbamoyl-D-allo-isoleucine. Preferably the contacting of the hydantoin with the D-hydantoinase is carried out under conditions permitting the simultaneous epimerization of the chiral center at C-5 of the hydantoin.

DETAILED DESCRIPTION

The present invention is directed to methods for the preparation of D-allo-isoleucine as a single diastereomer in high stereochemical purity and with a yield that can approach 100% of theoretical. The methods of the invention are based on the use of a stereoselective enzymatic reaction catalyzed by a D-hydantoinase, in which the hydantoin of L-isoleucine serves as the precursor. The hydantoin of L-isoleucine is prepared from the readily available L-isoleucine by methods well-known in the prior art. For example, L-isoleucine can be reacted with potassium cyanate as described by Garcia and Azerad [Tetrahedron: Asymmetry, vol. 8, pp. 85–92 (1997), hereby incorporated by reference] in an aqueous solution with heating, to afford the corresponding hydantoin in a yield greater than 90%. During the formation of the hydantoin, from L-isoleucine, either partial or complete epimerization of the chiral center at C-2 of isoleucine (C-5 of the hydantoin) may occur. An advantage of the method of the present invention is that all subsequent steps in the method may be carried out as described herein, irrespective of whether or not such epimerization occurs. The isoleucine hydantoin can be recovered prior to further reaction, if desired, by crystallization from water or water-alcohol mixtures, by precipitation from the reaction mixture after concentration, by chromatography, or other methods known to those skilled in the art.

The L-isoleucine hydantoin is then contacted with a D-hydantoinase under conditions permitting the epimerization of the hydantoin at the 5-position. As referred to herein, "epimerization of the hydantoin at the 5-position" means interconversion of the R and S absolute configurations of the chiral center at C-5 of the hydantoin, as shown in Scheme 1, below.

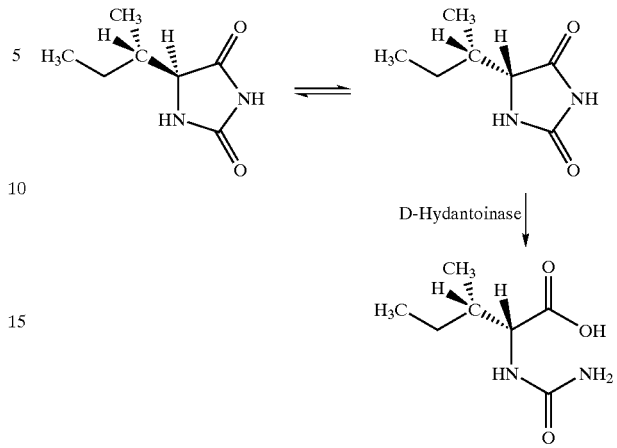

Scheme 1

In the practice of this invention, one condition useful for epimerization of the hydantoin at the 5-position is maintaining a pH of about 8.5 or higher. Epimerization of the hydantoin at the 5-position may also be achieved by contacting the hydantoin with an appropriate racemase, that is, an enzyme that can catalyze the epimerization at C-5 of the hydantoin. Only the chiral center at C-5 of the hydantoin is racemized under these conditions; the second chiral center in the molecule is unaffected.

When this racemization occurs in the presence of a D-hydantoinase, the L-isoleucine hydantoin establishes an equilibrium with the D-allo-isoleucine hydantoin, and the D-allo-isoleucine hydantoin is selectively hydrolyzed by the D-hydantoinase to form the N-carbamoyl-D-allo-isoleucine. As the D-allo-isoleucine hydantoin is depleted from the mixture by D-hydantoinase-catalyzed hydrolysis, the equilibrium between the L-isoleucine hydantoin and the D-allo-isoleucine hydantoin is re-established under the epimerizing conditions, continuously generating additional D-allo-isoleucine hydantoin for stereoselective hydrolysis by the D-hydantoinase enzyme. This continual supply of the hydantoin of D-allo-isoleucine occurs during the course of the reaction until substantially all of the L-isoleucine hydantoin has been converted to N-carbamoyl-D-allo-isoleucine. In this way, the reaction can be carried out to substantial Jun. 7, 2002 completion so that L-isoleucine hydantoin is converted to N-carbamoyl-D-allo-isoleucine. By the term "substantial completion" is meant that at least about 75%, preferably at least about 85%, and most preferably at least about 95%, of the L-isoleucine hydantoin is converted to N-carbamoyl-D-allo-isoleucine. The yield of N-carbamoyl-D-allo-isoleucine produced by the method of the present invention can approach 100% of theoretical, given sufficient reaction time and/or sufficient hydantoinase enzyme. The reaction can be monitored, if desired, by any method known in the art. An example of a method useful for monitoring the extent of reaction in the D-hydantoinase-catalyzed hydrolysis is thin layer chromatography on silica gel. Alternatively, high performance liquid chromatography can be used to monitor the extent of reaction.

In carrying out the D-hydantoinase catalyzed conversion of L-isoleucine hydantoin to N-carbamoyl-D-allo-isoleucine, the pH of the reaction mixture is an important factor. The pH is adjusted such that epimerization at C-5 of the hydantoin can occur at a rate that is not too slow, yet the pH must not be so high that the D-hydantoinase enzyme is inactivated. Preferably, the pH of the reaction mixture is in the range of from about 8.5 to about 11.5, and more preferably the pH is in the range of from about 8.7 to about 10.5. The D-hydantoinase catalyzed conversion of L-isoleucine hydantoin to N-carbamoyl-D-allo-isoleucine can be carried out over a wide range of temperatures, depending on the stability and activity of the D-hydantoinase. Preferably, the reaction is carried out at a temperature of from about 10° C. to about 80° C., and more preferably the reaction is carried out at a temperature of from about 30° C. to about 75° C.

In carrying out the hydantoinase-catalyzed hydrolysis step, either immobilized or non-immobilized D-hydantoinase can be used. Both immobilized and non-immobilized D-hydantoinases are available. For example, immobilized D-hydantoinase (product number 1582194, carrier fixed) is available from BioCatalytics, Inc. Pasadena, Calif. Alternatively, BioCatalytics, Inc, also sells a non-immobilized D-hydantoinase under the product number D-HYD2.

The L-isoleucine hydantoin can be epimerized, if desired, prior to reaction with a D-hydantoinase, to produce a mixture of epimeric D-and L-hydantoins. Such epimerization can be carried out in the presence of a base and under conditions such that only the chiral center at the 5-position of the hydantoin is epimerized; the second chiral center in the molecule is unaffected. Bases useful for the epimerization of the L-isoleucine hydantoin include sodium hydroxide, potassium hydroxide, ammonium hydroxide, sodium carbonate, potassium carbonate, secondary amines, tertiary amines, and the like. The epimerization can be carried out at room temperature or below, or the epimerization can be accelerated by heating, if desired. If heating is desired, a typical temperature for the epimerization is in the range of from about 40° C. to about 100° C., and more preferably from about 60° C. to about 100° C. After epimerization has been carried out, the epimerized hydantoin is then contacted with a D-hydantoinase in the presence of water to carry out the stereoselective hydrolytic conversion as described above.

Irrespective of how a D-hydantoinase is discovered or generated, any D-hydantoinase that is capable of hydrolyzing the hydantoin of D-allo-isoleucine, but not the hydantoin of L-isoleucine, may be used in the practice of this invention. A number of D-hydantoinases useful in the practice of this invention are known in the prior art. Example of D-selective hydantoinases that may be used in the invention include D-hydantoinase I and D-hydantoinase II, which are available commercially from BioCatalytics, Inc, (Pasadena, Calif.). The use of these hydantoinases has been described by Keil et al [Tetrahedron: Asymmetry, vol. 6, pp. 1257–1260 (1995)]. A number of other hydantoinases that are useful in the practice of this invention have been described by Syldakt and Wagner in Biocatalytic Production of Amino Acids and Derivatives, Chapter 5, pp.75–128, D. Rozzell and F. Wagner, eds., Hanser publishers, Munich, 1992, hereby incorporated by reference. Hydantoinases useful in the practice of this invention may also be discovered by screening or developed using various mutagenesis and screening procedures. Such mutagenesis and screening procedures are known in the art by names such as directed evolution, shuffling, molecular breeding, gene reassembly, gene redesign, and the like.

Decarbamoylation of the N-carbamoyl-D-allo-isoleucine can be accomplished either chemically or enzymatically by any methods known in the prior art. One chemical method of decarbamoylation useful in the practice of this invention involves the use of nitrous acid. This method has been described by Keil et al [Tetrahedron: Asymmetry, vol. 6, pp. 1257–1260 (1995)], and references therein. Enzymatic methods for decarbamoylation are also known. One method useful in the practice of this invention involves the use of a decarbamoylase enzyme. This method has been described generally for other D-amino acids by Nanba et al., U.S. Pat. No. 5,565,344, hereby incorporated in its entirety by reference. It is also possible to carry out the D-hydantoinase-catalyzed hydrolysis and the enzyme-catalyzed decarbamoylation of the N-carbamoyl-D-allo-isoleucine in a single reaction by incorporating both enzymes in the same reaction mixture. For example, L-isoleucine hydantoin can be reacted in the presence of a D-hydantoinase and a decarbamoylase at a pH preferably ranging from about 8 to about 10, more preferably from about 8.3 to about 9.5, and at a temperature preferably ranging from about 20° C. to about 70° C., more preferably from about 30° C. to about 60° C.

Following decarbamoylation, the product D-allo-isoleucine can be isolated by any of the know methods for amino acid isolation, including ion exchange chromatography, crystallization from a concentrated aqueous solution or an aqueous/alcohol mixture, or precipitation with ethanol or acetone. D-allo-isoleucine may be isolated as a zwitterion, or, if desired, D-allo-isoleucine may also be crystallized as a salt. Salts useful for the crystallization of D-allo-isoleucine include, but are not limited to, dicyclcohexylammonium, dibenzylammonium, diethylammonium, and the like.

The invention will now be described by the following examples, which are presented here for illustrative purposes and are not intended to limit the scope of the invention.

EXAMPLE 1

Synthesis of the Hydantoin of L-isoleucine

L-Isoleucine (131 g, 1 mol) and potassium cyanate (81 g, 1 mol) were mixed in 500 ml of $H_2O$ and the mixture was stirred at room temperature until the L-isoleucine was dissolved. The resulting solution was treated with 150 ml of hydrochloric acid (36–38%) and a white precipitate formed. The mixture was then heated to a clear solution. After the solution was cooled to room temperature, the product was isolated via filtration as a crystalline solid (148 g, 95% yield).

EXAMPLE 2

Conversion of L-isoleucine hydantoin to N-carbamoyl-D-allo-isoleucine using a D-hydantoinase The L-isoleucine hydantoin (2 g), prepared as described in Example 1, was suspended in 100 ml of glycine-NaOH buffer (0.1 M, pH=8.5) containing 1 mM of $MnCl_2$ under nitrogen. When the mixture was heated to 50° C., the hydantoin was dissolved. Hydantoinase I (1 g, BioCatalytics, Inc., Pasadena, Calif. USA, catalog number 1582194, carrier fixed) was added, and the mixture was stirred at 50° C. under nitrogen. The pH was controlled at 8.5 by the addition of a 1 N NaOH solution. The reaction was monitored by HPLC [Column: ChrownPack CR(+); eluent: $H_2O$]. After the hydantoin was completely converted (24 hrs), the mixture was filtered. The analytical yield of N-carbamoyl-D-allo-isoleucine was near 100%. To recover the product, the filtrate was acidified to pH=1 to 2 and maintained at room temperature. The resulting precipitate was separated via filtration and dried to give the product as a colorless solid (1.4 g, 63% yield).

EXAMPLE 3

Alternative Conversion of L-isoleucine Hydantoin to N-carbamoyl-D-allo-isoleucine Using a D-hydantoinase The L-isoleucine hydantoin (2 g), prepared as described in Example 1, was suspended in 100 ml of glycine-NaOH buffer (0.1 M, pH=9.0) containing 1 mM of $MnCl_2$ under nitrogen. When the mixture was heated to 50° C., the hydantoin was dissolved. Hydantoinase II (0.05 g, BioCatalytics, Inc., Pasadena, Calif. USA, catalog number HYD-2) was added, and the mixture was stirred at 50° C. under nitrogen. The pH was controlled at 9.0 by the addition of a 3 N ammonium hydroxide solution. The reaction was monitored by HPLC [Column: ChrownPack CR(+); eluent: $H_2O$]. After the hydantoin was completely converted (24 hrs), the mixture was filtered. The filtrate was acidified to pH=1 to 2 and maintained at room temperature. The resulting precipitate was separated via filtration and dried to give the product as a colorless solid (1.5 g, 65% yield).

EXAMPLE 4

Decarbamoylation of N-carbamoyl-D-allo-isoleucine Using a Decarbamoylase Enzyme

The N-carbamoyl-D-allo-isoleucine (50 mg), prepared as described in Example 2, was dissolved in 20 ml of sodium phosphate buffer (0.1 M, pH=8.0) and 20 mg of decarbamoylase (BioCatalytics, Inc., Pasadena, Calif. USA, product number DECARB-1) was added to the mixture. The mixture was shaken at 40° C. The reaction was monitored by HPLC [Column: ChrownPack CR(+); eluent: 0.01 M $HClO_4$ solution]. When the reaction was complete, the resulting mixture was deposited on the DOWEX-50 ion exchange column. The column was washed with water and the pure D-allo-isoleucine was eluted with 0.01 N $NH_4OH$ solution and recovered by evaporation in vacuo (31 mg, 82% yield). The optical purity was >99% the single diastereomer of D-allo-isoleucine.

EXAMPLE 5

Alternative Decarbamolylation of N-carbamoyl-D-allo-isoleucine Using a Decarbamoylase Enzyme The procedure of Example 4 was repeated except that the pH used was 7.5. D-allo-isoleucine was isolated in 80% yield.

EXAMPLE 6

Alternative Decarbamolylation of N-carbamoyl-D-allo-isoleucine Using Nitrous Acid The N-carbamoyl-D-allo-isoleucine (87 mg, 0.5 mmol), prepared as described in Example 2, was suspended in 20 ml of 3.5 N hydrochloric acid. The mixture was cooled to 0° C. and 0.5 mmol of sodium nitrite was added. The reaction was monitored by HPLC [Column: ChrownPack CR(+); eluent: 0.01 M $HClO_4$ solution]. When the conversion was close to 100%, the mixture was neutralized with 4 N NaOH solution. The resulting mixture was deposited on the DOWEX-50 ion exchange column. The column was washed with water, and the pure D-allo-isoleucine was eluted with 0.01 N $NH_4OH$ solution and recovered by evaporation in vacuo (28 mg, 43% yield).

EXAMPLE 7

Single-pot Conversion of L-isoleucine Hydantoin to D-allo-isoleucine Using a D-hydantoinase and Decarbamoylase The L-isoleucine hydantoin (2 g), which is prepared as described in Example 1, is suspended in 100 ml of glycine-NaOH buffer (0.1 M, pH 9.0) containing 1 mM of $MnCl_2$ under nitrogen, and the mixture is heated 50° C. Hydantoinase II (0.05 g, BioCatalytics, Inc., Pasadena, Calif. USA, catalog number HYD-2) is added, and the mixture is stirred at 50° C. under nitrogen. The pH is controlled at 9.0 by the addition of a 3 N ammonium hydroxide solution. The progress of the reaction is monitored by HPLC [Column: ChrownPack CR(+); eluent: $H_2O$]. After the hydantoin is completely converted (24 hrs), the pH of the solution is adjusted to 8.0 by the addition of 6 N HCl. Twenty milligrams of decarbamoylase (BioCatalytics, Inc., Pasadena, Calif. USA, product number DECARB-1) is added to the mixture. The mixture is stirred at 40° C. and monitored by HPLC [Column: ChrownPack CR(+); eluent: 0.01 M $HClO_4$ solution]. When the reaction is complete, the resulting mixture is deposited on the DOWEX-50 ion exchange column. The column is washed with water and the pure D-allo-isoleucine eluted with 0.01 N $NH_4OH$ solution and recovered by evaporation in vacuo.

EXAMPLE 8

Alternative Single-pot Conversion of L-isoleucine hydantoin to D-allo-isoleucine Using a D-hydantoinase and Decarbamoylase The L-isoleucine hydantoin (2 g), which is prepared as described in Example 1, is suspended in 100 ml of glycine-NaOH buffer (0.1 M, pH=8.3) containing 1 mM of $MnCl_2$ under nitrogen, and the mixture is heated to 40° C. Hydantoinase II (0.05 g, BioCatalytics, Inc., Pasadena, Calif. USA, catalog number HYD-2) and decarbamoylase (0.05 g, BioCatalytics, Inc., Pasadena, Calif. USA, product number DECARB-1) are added, and the mixture is stirred at 40° C. under nitrogen. The pH is controlled at 8.3 by the addition of a 3 N ammonium hydroxide solution. The progress of the reaction is monitored by HPLC. L-isoleucine hydantoin is converted to D-allo-isoleucine under these conditions.

The preceding description has been presented with reference to presently preferred embodiments of the invention. Workers skilled in the art and technology to which this invention pertains will appreciate that alterations and changes in the described methods may be practiced without meaningfully departing from the principal, spirit and scope of this invention. Accordingly, the foregoing description should not be read as pertaining only to the precise methods described, but rather should be read consistent with and as support to the following claims which are to have their fullest and fair scope.

What is claimed is:

1. A method for producing D-allo-isoleucine comprising:
   converting L-isoleucine to the corresponding hydantoin;
   contacting a mixture containing the hydantoin with a D-hydantoinase to a stereoselectively hydrolyze any D-allo-isoleucine hydantoin in the mixture to the corresponding N-carbamoyl-D-allo-isoleucine; and
   decarbamoylating the N-carbamoyl-D-allo-isoleucine to produce D-allo-isoleucine.

2. The method of claim 1, wherein the contacting of the hydantoin with a D-hydantoinase is carried out under conditions permitting the simultaneous epimerization of the chiral center at C-5 of the hydantoin.

3. The method of claim 2, wherein the simultaneous epimerization of the chiral center at C-5 of the hydantoin is carried out at a pH of about 8.5 or higher.

4. The method of claim 2, wherein the simultaneous epimerization of the chiral center at C-5 of the hydantoin is carried out at a pH ranging from about 8.5 to about 9.5.

5. The method of claim 2, wherein at least about 75% of the L-isoleucine hydantoin is converted to N-carbamoyl-D-allo-isoleucine.

6. The method of claim 2, wherein at least about 85% of the L-isoleucine hydantoin is converted to N-carbamoyl-D-allo-isoleucine.

7. The method of claim 2, wherein at least about 95% of the L-isoleucine hydantoin is converted to N-carbamoyl-D-allo-isoleucine.

8. The method of claim 1, wherein the decarbamoylation is carried out using a decarbamoylase enzyme.

9. A method for producing D-allo-isoleucine comprising:
epimerizing L-isoleucine to a mixture of L-isoleucine and D-allo-isoleucine;
converting the mixture of L-isoleucine and D-allo-isoleucine to the corresponding hydantoin mixture containing L-isoleucine hydantoin and D-allo-isoleucine hydantoin;
contacting the hydantoin mixture with a D-hydantoinase under conditions permitting the stereoselective hydrolysis of only the D-allo-isoleucine hydantoin to the corresponding N-carbamoyl-D-allo-isoleucine; and
decarbamoylating the N-carbamoyl-D-allo-isoleucine to product D-allo-isoleucine.

10. A method for producing N-carbamoyl-D-allo-isoleucine comprising:
converting L-isoleucine to the corresponding hydantoin; and
contacting a mixture containing the L-isoleucine hydantoin with a D-hydantoinase to stereoselectively hydrolyze any D-allo-isoleucine hydantoin in the mixture to the corresponding N-carbamoyl-D-allo-isoleucine.

11. The method of claim 10, wherein the contacting of the hydantoin with a D-hydantoinase is carried out under conditions permitting the simultaneous epimerization of the chiral center at C-5 of the hydantoin.

12. The method of claim 11, wherein the simultaneous epimerization of the chiral center at C-5 of the hydantoin is carried out at a pH of about 8.5 or higher.

13. The method of claim 11, wherein the simultaneous epimerization of the chiral center at C-5 of the hydantoin is carried out at a pH ranging from about 8.5 to about 9.5.

14. The method of claim 11, wherein at least about 75% of the L-isoleucine hydantoin is converted to N-carbamoyl-D-allo-isoleucine.

15. The method of claim 11, wherein at least about 85% of the L-isoleucine hydantoin is converted to N-carbamoyl-D-allo-isoleucine.

16. The method of claim 11, wherein at least about 95% of the L-isoleucine hydantoin is converted to N-carbamoyl-D-allo-isoleucine.

17. The method of claim 8, wherein the D-hydantoinase and decarbamoylase are present together in the mixture.

* * * * *

UNITED STATES PATENT AND TRADEMARK OFFICE
CERTIFICATE OF CORRECTION

PATENT NO.    : 6,822,116 B2
DATED         : November 23, 2004
INVENTOR(S)   : J. David Rozzell It is certified that error appears in the above-identified patent and that said Letters Patent is hereby corrected as shown below:

Column 2,
Line 44, after "to" delete "a".

Signed and Sealed this

Twenty-seventh Day of September, 2005

JON W. DUDAS
*Director of the United States Patent and Trademark Office*